(12) United States Patent
Cheng (10) Patent No.: US 7,551,950 B2
(45) Date of Patent: Jun. 23, 2009

(54) OPTICAL APPARATUS AND METHOD OF USE FOR NON-INVASIVE TOMOGRAPHIC SCAN OF BIOLOGICAL TISSUES

(75) Inventor: Xuefeng Cheng, Sunnyvale, CA (US)

(73) Assignee: O2 Medtech, Inc,., Los Altos, CA (US)

( * ) Notice: Subject to any disclaimer, the term of this patent is extended or adjusted under 35 U.S.C. 154(b) by 880 days.

(21) Appl. No.: 10/877,977

(22) Filed: Jun. 29, 2004

(65) Prior Publication Data

US 2006/0015021 A1    Jan. 19, 2006

(51) Int. Cl.
   *A61B 5/1455*    (2006.01)
(52) U.S. Cl. .................. 600/310; 600/322; 600/407
(58) Field of Classification Search ................. 600/310, 600/322, 323, 473, 476
   See application file for complete search history.

(56) References Cited

U.S. PATENT DOCUMENTS

| 5,477,051 | A  | 12/1995 | Tsuchiya     |
| 5,553,614 | A  | 9/1996  | Chance       |
| 6,195,574 | B1 | 2/2001  | Kumar et al. |
| 6,246,892 | B1 | 6/2001  | Chance       |
| 6,493,565 | B1 | 12/2002 | Chance et al.|
| 6,516,209 | B2 | 2/2003  | Cheng et al. |
| 6,549,284 | B1 | 4/2003  | Boas et al.  |
| 6,597,931 | B1 | 7/2003  | Cheng et al. |
| 2001/0038454 | A1 | 11/2001 | Tsuchiya |
| 2002/0033454 | A1 | 3/2002 | Cheng et al. |
| 2002/0035317 | A1 | 3/2002 | Cheng et al. |
| 2002/0037095 | A1 | 3/2002 | Cheng |
| 2002/0058865 | A1 | 5/2002 | Cheng et al. |
| 2004/0162468 | A1 | 8/2004 | Cheng et al. |

FOREIGN PATENT DOCUMENTS

WO    WO 02/12854 A2    2/2002

OTHER PUBLICATIONS

Michael R. Newman, "Pulse Oximetry: Physical Principles, Technical Realization and Present Limitations," Adv. Exp. Med. Biol., 220:135-144 (1987).
John W. Severinghaus, "History and recent developments in pulse oximetry," Scan. J. Clin. And Lab. Investigations, 53:105-111 (1993).

*Primary Examiner*—Eric F Winakur
*Assistant Examiner*—Etsub D Berhanu
(74) *Attorney, Agent, or Firm*—Cooper & Dunham LLP (57) ABSTRACT

The present invention relates to a non-invasive optical system equipped with optical tomographic scanning method and algorithm for quantifying scattering and absorption properties and chromophore concentrations of highly scattering medium such as biological tissues, for 3D mapping and imaging reconstruction of the spatial and temporal variations in such properties. The invention further relates to a method and an apparatus for simultaneous measurement of concentrations of biochemical substances and blood oxygen saturation inside a biological tissue and arterial blood.

48 Claims, 9 Drawing Sheets

OPTICAL APPARATUS AND METHOD OF USE FOR NON-INVASIVE TOMOGRAPHIC SCAN OF BIOLOGICAL TISSUES

FIELD OF THE INVENTION

The present invention relates to methods and optical imaging systems for images of spatial or temporal distribution of chromophores or properties thereof in a physiological medium. The optical imaging system is useful for the non-invasive measurement of various physiological properties in animal and human subjects and in particular, is useful in determining blood oxygen saturation of both tissue and arteries.

BACKGROUND OF THE INVENTION

Near-infrared spectroscopy has been used for non-invasive measurement of various physiological properties in animal and human subjects. The basic principle underlying the near-infrared spectroscopy is that a physiological medium, such as a tissue, includes a variety of light-absorbing chromophores and light-scattering substances which can interact with low energy near-infrared photons transmitted thereto and traveling therethrough. For example, deoxygenated and oxygenated hemoglobins in human blood are the most dominant chromophores in the spectrum range of 700 nm to 900 nm. Therefore, the near-infrared optical spectroscopy has been applied to non-invasively measure oxygen levels in the physiological medium in terms of tissue hemoglobin oxygen saturation (or simply oxygen saturation hereafter). Technical background for the near-infrared spectroscopy and diffuse optical imaging has been discussed in, e.g., Neuman, M. R., "Pulse Oximetry: Physical Principles, Technical Realization and Present Limitations," *Adv. Exp. Med. Biol.*, 220:135-144, (1987), and Severinghaus, J. W., "History and Recent Developments in Pulse Oximetry," *Scan. J. Clin. And Lab. Investigations*, 53:105-111, (1993).

Various techniques have been developed for the non-invasive near-infrared spectroscopy, including time-resolved spectroscopy (TRS), phase modulation spectroscopy (PMS), and continuous wave spectroscopy (CWS). (Chance, U.S. Pat. No. 5,553,614; Chance, U.S. Pat. No. 6,246,892; and Tsuchiya, U.S. Pat. No. 5,477,051). The TRS and PMS are generally used to solve the photon diffusion equation, to obtain the spectra of absorption coefficients and reduced scattering coefficients of the physiological medium, and to estimate concentrations of the oxygenated and deoxygenated hemoglobins and oxygen saturation. To the contrary, the CWS method cannot distinguish the light scattering and absorption properties and has generally been used to calculate relative values of or changes in the concentrations of the oxygenated or deoxygenated hemoglobins. (Cheng et al., U.S. Pat. No. 6,516,209; Cheng et al., U.S. Pat. No. 6,597,931).

PMS has been known as the most cost effective method to quantify the scattering and absorption properties of turbid medium compared to TRS. Various methods have been developed to calculate the absorption and scattering properties. Most methods have been using both the amplitude and phase measurement and using photon diffusion equations. However, there are problems involving in these methods. First, they are usually very noisy since the amplitude measurement is affected by many elements, such as source, detector drift, sensor attachment, etc. Second, there is no analytical inverse solution for the diffusion equation which results in it being hard to conduct accurate calculation. Finally, despite their capability of providing averaged quantitative hemoglobin concentrations and the oxygen saturation, the general problem of the TRS and PMS is that it is difficult to quantify concentrations of chromophores of a localized position inside tissues, such as the cortical tissue inside the head. (Cheng et al., U.S. Pat. No. 6,516,209; Cheng et al., U.S. Pat. No. 6,597,931). However, such localized information is usually critical for clinical and medical applications, such as cortex perfusion monitoring, diagnosis of hematoma, stroke, organ function monitoring, etc.

Various imaging approaches have been explored for imaging biological tissues using near-infrared photons. Nevertheless, there is no existing method which worked effectively, especially for the applications where only back reflected photons are detectable and transmitted photons are too weak to be detected, such as measurement on head or chest. The major challenge has been due to the scattering effect. Photons quickly lose their original travel direction and become randomized, and photon density exponentially decreases as photons travel deeper into the tissue. As a result, the detected photons always come from a volume of tissue, and the majority of which always comes from the superficial part of the tissue. Accordingly, in order to obtain properties of a local region inside tissue, one needs to deconvolve the contribution of all local region tissue to the signal.

SUMMARY OF THE INVENTION

The present invention generally relates to optical imaging systems, optical probes, algorithm and methods thereof for providing two- or three-dimensional images of spatial or temporal variations in the absorption properties of highly scattering physiological media. Specifically, the present invention utilizes formulas and algorithms that allow the determination of absorption properties of highly scattering physiological media based on phase only measurements.

One aspect of the present invention relates to a method of using a phase only measurement for quantifying at least one of scattering property, absorption coefficient or chromophore concentrations of a physical medium, said method comprising the steps of:

(a) introducing into said physical medium, at a first site, an input modulated signal with a modulation frequency ($F_n$);

(b) detecting, at a second site, an output modulated signal migrated over a migration path in said physical medium from said input modulated signal;

(c) comparing said output modulated signal with said input modulated signal and measuring therefrom a phase shift ($\phi$) between said input modulated signal and said output modulated signal;

(d) repeating steps (a)-(c) at two or more modulation frequencies and calculating an average scattering property and absorption coefficient of said physical medium using the following equation:

$$\phi = \left(\sum_{n=0}^{1} a_n \mu_s'^n\right) \mu_a^{-1} + \left(\sum_{n=0}^{2} b_n \mu_s'^n\right) \mu_a^{-0.5} + \sum_{n=0}^{1} c_n \mu_s'^n$$

wherein $\mu_a$ is the absorption coefficient, $\mu_s'$ is the effective scattering property of said physical medium, and $a_n$, $b_n$, and $c_n$ are parameters determined by said modulation frequency ($F_n$) and a distance (D) between said first site and said second site using a fitting algorithm.

Another aspect of the present invention relates to a method of using an optical imaging system, which uses phase only measurement for quantifying scattering absorption properties, for non-invasive tomographic scan of highly scattering medium using back scattered photons.

Another aspect of the present invention relates to a method and an optical imaging system for simultaneous measurement of concentrations of biochemical substances and blood oxygen saturation inside tissue and artery. The chromophore concentrations such as oxy-, deoxy-hemoglobin of both tissue and arterial blood can be simultaneously determined.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The primary object of present invention is to provide a non-invasive optical system, an optical scanning method, such as tomographic scanning method, and algorithm for quantifying scattering and absorption properties and chromophore concentrations of highly scattering medium, such as biological tissues, for three-dimensional (3D) mapping and imaging reconstruction of the spatial and temporal variations in such properties.

One aspect of the present invention relates to a non-invasive optical system and a method for quantifying the scattering and absorption properties of highly scattering medium. The method includes the steps of taking phase-only measurement and relating the phase-only measurement to the scattering and absorption properties of the scattering medium using a special formula.

Another aspect of the present invention relates to a non-invasive optical system and a method for tomographic scanning of highly scattering medium. The method includes the steps of measuring back scattered diffuse photons and reconstructing two-dimensional (2D) and three-dimensional (3D) images of the absorption and scattering properties of the highly scattering medium using an algorithm based on the phase-only measurements.

Yet another aspect of the present invention relates to a non-invasive optical system and a method for simultaneous determination of the absolute values of concentrations of the hemoglobins (both of deoxy- and oxy-hemoglobin) and oxygen saturation (a ratio of oxy-hemoglobin concentration to total hemoglobin concentration which is a sum of the concentrations of oxy- and deoxy-hemoglobin) in brain tissues and in arterial blood.

Yet another aspect of the present invention relates to a method of applying a non-invasive optical system to a biological tissue for various medical applications, such as monitoring concentrations of oxygenated hemoglobin, deoxygenated hemoglobin and their ratio thereof; determining a presence of an ischemic condition over a finite area of said biological tissue; detecting the location of an artery; and determining the presence of tumor cells over a finite area of said biological tissue, etc.

The biological tissue comprises at least one of organ, tissue, or body fluid. For example, the biological tissue may be brain, heart, kidney, liver and vascular tissue which includes artery, vein, and capillary. The biological tissue may further include transplanted cells.

As used herein, a "chromophore" means any substance in a physiological medium which can interact with electromagnetic waves transmitting therethrough. Such chromophore may include solvents of a medium, solutes dissolved in the medium, and/or other substances included in the medium. Specific examples of such chromophores may include, but not limited to, cytochromes, enzymes, hormones, proteins, cholesterols, lipids, apoproteins, chemotransmitters, neurotransmitters, carbohydrates, cytosomes, blood cells, cytosols, water, oxygenated hemoglobin, deoxygenated hemoglobin, and other materials present in the animal or human cells, tissues or body fluid. The "chromophore" may also include any extra-cellular substance which may be injected into the medium for therapeutic or imaging purposes and which may interact with electromagnetic waves. Typical examples of such chromophores may include, but not limited to, dyes, contrast agents, and/or other image-enhancing agents, each of which exhibits optical interaction with electromagnetic waves having wavelengths in a specific range.

As used herein, the term "property" of the chromophore refers to intensive property thereof such as concentration of the chromophore, a sum of concentrations thereof, a ratio thereof, and the like. "Property" may also refer to extensive property such as, e.g., volume, mass, weight, volumetric flow rate, and mass flow rate of the chromophore.

As used herein, the term "electromagnetic waves" may include sound waves, near-infrared rays, infrared rays, visible light rays, ultraviolet rays, lasers, and/or photons.

As used herein, the term "distribution" refers to two-dimensional or three-dimensional distribution of the chromophores or their properties. The "distribution" may be measured or estimated in a spatial and/or temporal domain.

Unless otherwise defined, all technical and scientific terms used herein have the same meaning as commonly understood and/or used by one of ordinary skill in the art to which this invention belongs. Although methods and materials similar or equivalent to those described herein can be applied and/or used in the practice of or testing the present invention, suitable methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Figure 1:
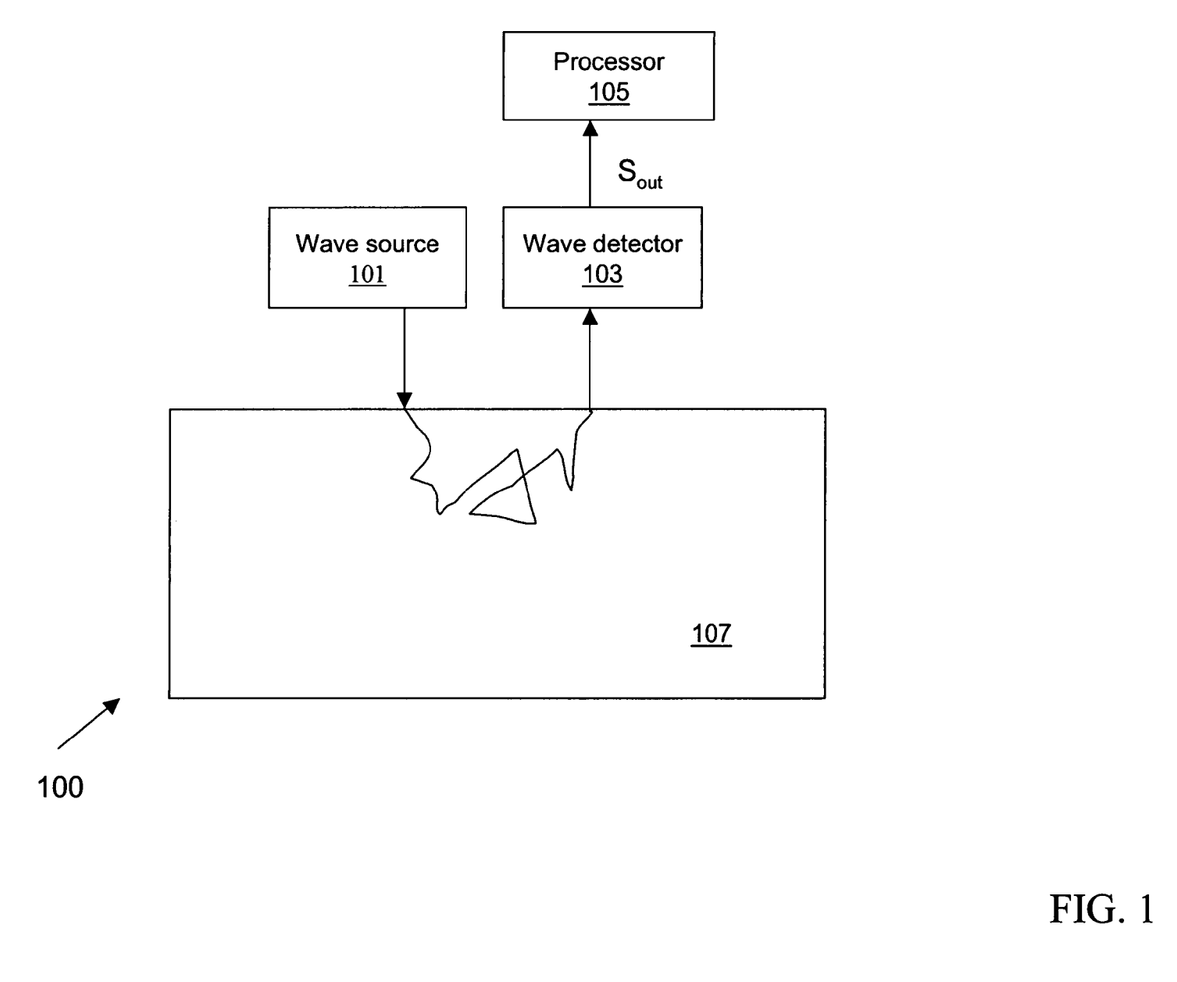
FIG. 1 depicts an exemplary optical imaging system set-up with a wave source, a wave detector and a signal processor.

FIG. 1 depicts a simplified optical imaging system 100 that contains a wave source 101, a wave detector 103, and a signal processor 105. The wave source 101 irradiates electromagnetic source waves into a physiological medium 107. The wave detector 103 detects the electromagnetic waves at a distance from the wave source 101 and generates output signals $S_{out}$ in response thereto. The signal processor 105 then processes the signals using a predetermined algorithm and provides information about the distribution of chromophores in the physiological medium 107.

The wave source 101 of the present invention is generally arranged to form optical coupling with the physiological medium 107 and to irradiate electromagnetic waves thereto. Any wave sources may be employed in the optical imaging system 100 to irradiate electromagnetic waves having preselected wavelengths, e.g., in the ranges from 100 nm to 5,000 nm, from 300 nm to 3,000 nm, in the "near-infrared" range from 500 nm to 2,500 nm, or in a most preferred range of 600-900 nm. In one embodiment, the wave source 101 is arranged to irradiate near-infrared electromagnetic waves having at least wavelengths of about 690 nm, about 780 nm or about 830 mm. The wave source 101 may also irradiate electromagnetic waves having different wave characteristics such as different wavelengths, phase angles, frequencies, amplitudes, harmonics, etc. Typically, the intensity of the electromagnetic source waves can be modulated at two or more frequencies (Fn) that are higher than 50 MHz, for example, the electromagnetic source waves are modulated at frequencies at 100 MHz, 300 MHz, and/or 500 MHz, etc. Alternatively, the wave source 101 may irradiate electromagnetic waves in which identical, similar or different signal waves are superposed on carrier waves with similar or mutually distinguishable wavelengths, frequencies, phase angles, amplitudes or harmonics.

The wave detector 103 is preferably arranged to detect the aforementioned electromagnetic waves and to generate the output signal in response thereto. The wave detector 103 is placed at a distance (D) from the wave source 101. The distance (D) can be from 0.1 cm to 30 cm, preferably, from 0.1 cm to 20 cm. Any wave detector 103 may be used in the optical imaging system 100 as long as it has appropriate detection sensitivity to the electromagnetic waves having wavelengths in the foregoing ranges. The wave detector 103 may also be constructed to detect electromagnetic waves which may have any of the foregoing wave characteristics. In one embodiment, the wave detector 103 detects multiple sets of electromagnetic waves irradiated by multiple wave sources 101 and generate multiple output signals accordingly.

Figure 2:
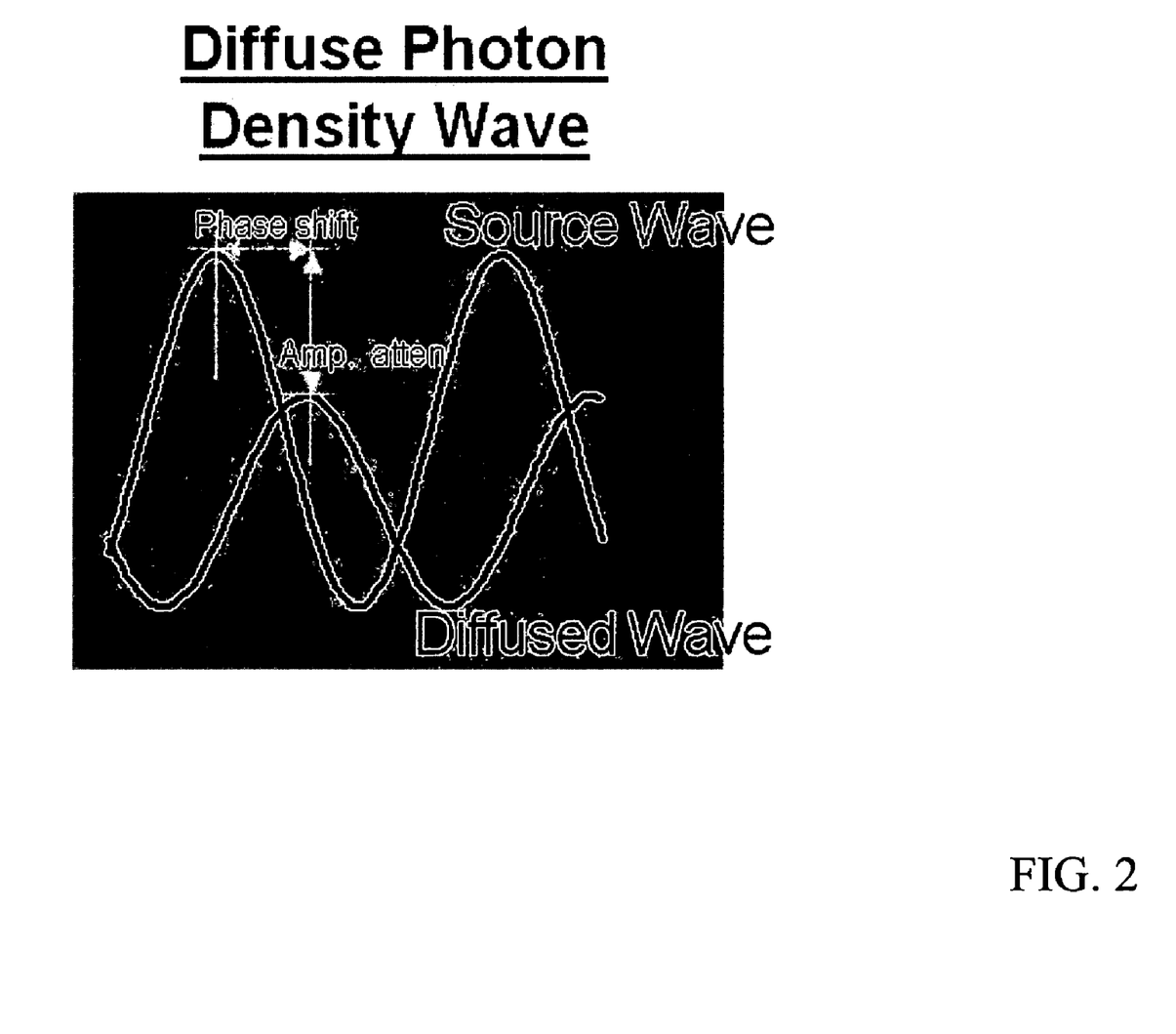
FIG. 2 shows the difference in amplitude and phase measurement between a source wave and a diffused wave.

The signal processor 105 includes an algorithm for determining the absolute values of the chromophore concentrations (or their ratios) based on the phase shift and other variables and/or parameters FIG. 2 shows the wave characteristics before (source wave) and after (diffuses wave) traveling through a physiological medium. Typically, the phase and amplitude of the source wave change due to the scattering effect and absorption of the physiological medium. Referring back to FIG. 1, the wave detector 103 detects the phase shift of the received signal compared to the wave source at the different modulation frequencies. The phase measurements are then used to calculate the average scattering and absorption properties of the medium 107 to the magnetic wave along the path which has been passed by the detected magnetic waves. The calculation is based upon the following equation.

$$\phi = \left(\sum_{n=0}^{1} a_n \mu_s'^n\right)\mu_a^{-1} + \left(\sum_{n=0}^{2} b_n \mu_s'^n\right)\mu_a^{-0.5} + \sum_{n=0}^{1} c_n \mu_s'^n \quad (1)$$

wherein $\phi$ is the measured phase shift; $u_a$ is the absorption coefficient; $u_s'$ is the effective scattering properties of the medium. The parameters $a_n$, $b_n$, and $c_n$, only depend on the source-detector separation (D) and modulation frequency ($F_n$), and can be determined by using a fitting algorithm such as Monte Carlo simulation, which is a standard method to deal with multi-object interaction. The absorption and scattering properties of the medium are set to various numbers, and for each scattering and absorption a phase will be calculated. Each calculated phase and corresponding scattering and absorption property is then put into Equation (1) and formed into a group of linear equations to solve $a_n$, $b_n$, and $c_n$.

As an example, for modulation frequency of 150 MHz, when the separation of a source and a detector is 2 cm, the coefficients are:

$$\phi = (-0.0021\mu_s' - 0.0115)\mu_a^{-1} + \quad (2)$$
$$(-0.0012\mu_s'^2 + 0.594\mu_s' + 0.1297)\mu_a^{-0.5} - 0.0055\mu_s' + 0.016$$

The modulation can then be changed to a different frequency such as 120 MHz, 140 MHz, etc. while the source-detector separation remains the same, 2 cm, then a series of equations will be obtained, from which, the two unknowns of scattering and absorption coefficients can then be solved. If multiple wavelengths are applied, then the absorption spectrum will be obtained and the concentration of chromophores can be obtained.

Figure 3A:
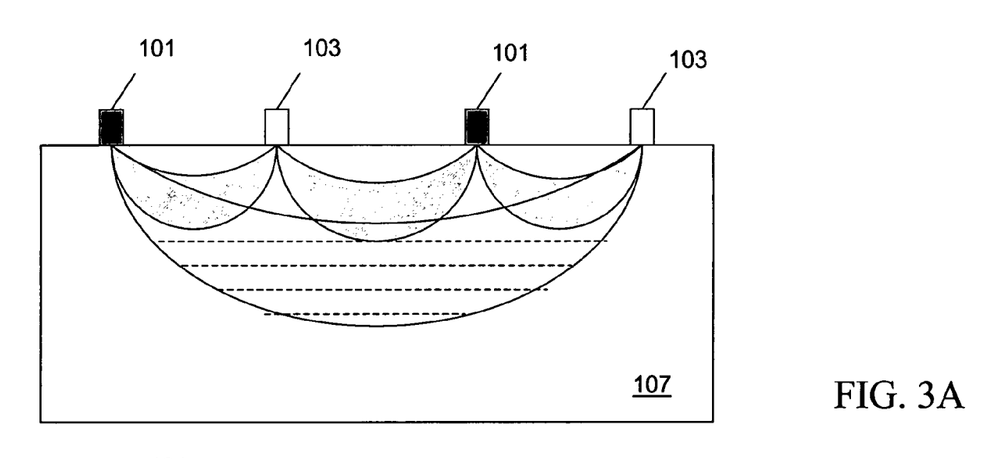
FIGS. 3A and 3B depict different wave source/wave detector arrangement and the scanned areas in each arrangements.
Figure 3B:
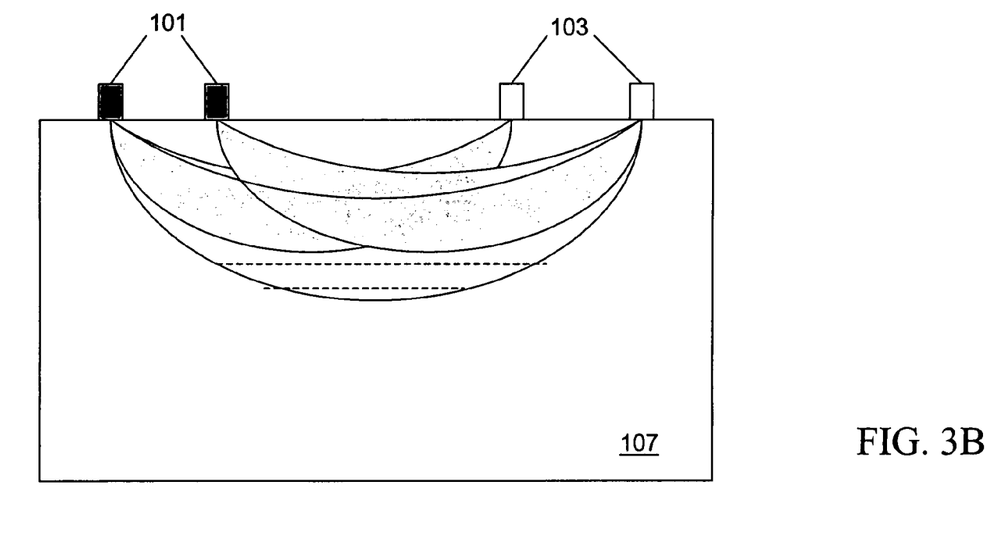

FIGS. 3A and 3B depict an optical imaging system 200 having at least two wave sources 101 for irradiating electromagnetic waves into the physiological medium 107 and at least two detectors 103 for detecting electromagnetic waves and generating output signals in response thereto. The intensity of each wave source 101 is modulated at least at two different frequencies larger than 50 MHz. Each detector 103 detects the phase shift of the modulated wave from each source for each modulation frequency. For a given tissue and optical wavelength, the distance between the wave source 101 and the wave detector 103 determines the tissue region scanned by the light. The larger the source-detection separation, the larger the volume scanned.

Figure 4:
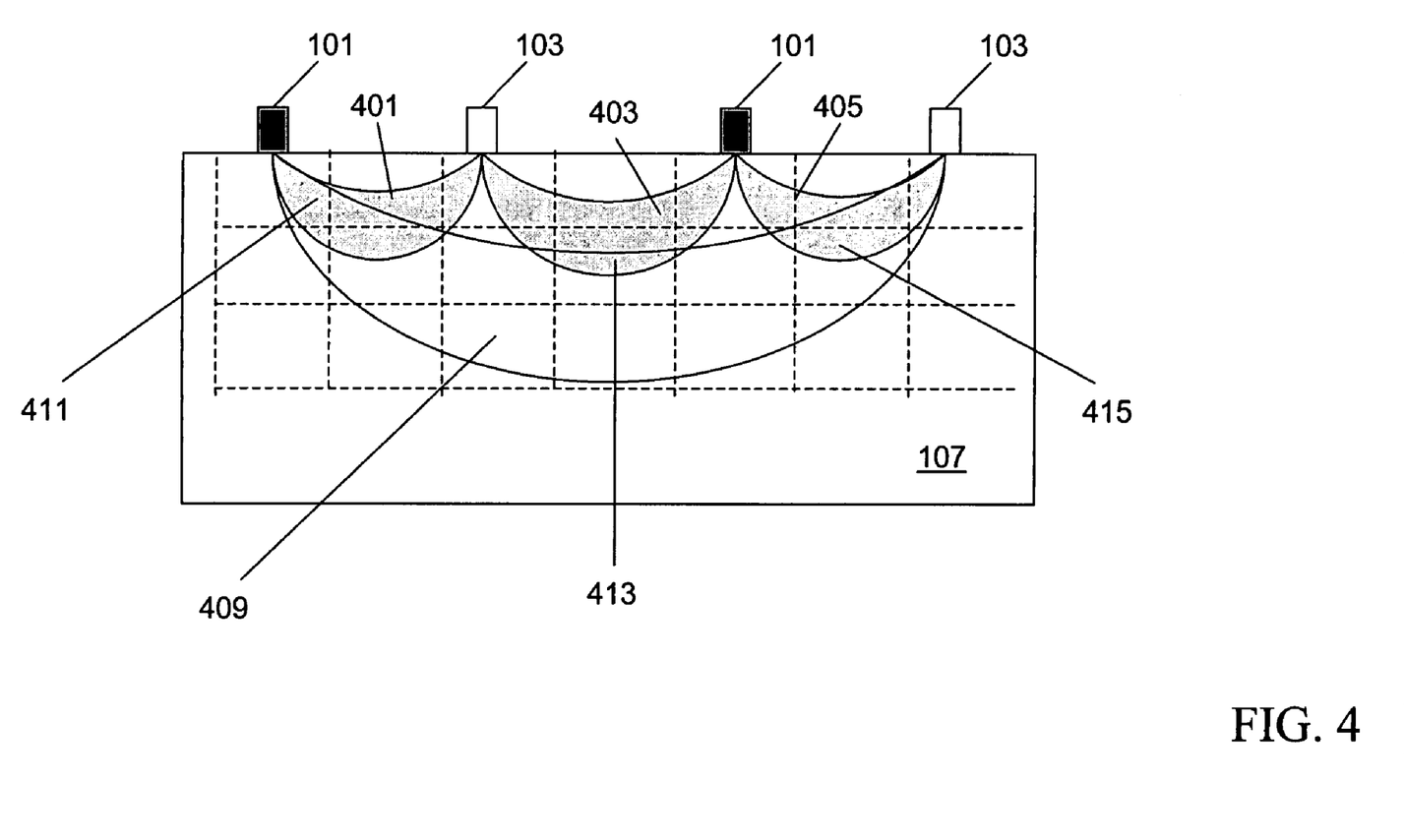
FIG. 4 depicts the volume elements in a scanned medium.

In this set up, each source/detector pair measures the absorption and scattering properties of the physiological medium 107 between the corresponding wave source 101 and the wave detector 103. As shown in FIG. 4, the physiological medium 107 is divided into a number of volume elements. Each measured optical property is the weighted summation of the optical properties of all the volume elements. As shown in the following:

$$\mu_a^i = w_1^i \mu_{a,1}^i + w_2^i \mu_{a,2}^i + w_3^i \mu_{a,3}^i + \ldots w_m^i \mu_{a,m}^i$$
$$\mu_s^i = w_1^i \mu_{s,1}^i + w_2^i \mu_{s,2}^i + w_3^i \mu_{s,3}^i + \ldots w_m^i \mu_{s,m}^i \quad (3)$$

i means the measurement of ith source-detector pair. $w_1^i$ is the weight of the first volume element corresponding to the ith source-detector pair, $w_2^i$ is the weight of the second volume element corresponding to the ith source-detector pair, and $w_m^i$ is the weight of the mth volume element corresponding to the ith source-detector pair. $w_1$ is calculated based upon the absorption and scattering properties obtained through measurement of the ith source-detector pair and based upon the forward calculation of photon diffusion or transportation equations. By solving the group of linear equations, the absorption and scattering properties of each volume element can be determined and the 2D and 3D images can be created by coding colors to the magnitude of the optical properties of each volume element.

A two source, two detector configuration with more than two modulation frequencies $>=50$ MHz and multiple optical wavelengths, can also perform depth or location resolved spectroscopy measurement. As shown in FIG. 4, the three source-detector pairs with smaller separation measure "above" areas 401, 403, and 405. The measurement with largest source-detector separation covers a "below" area 409. The "below" area 409 overlaps with the "above" areas 401, 403, and 405 in regions 411, 413, and 415, respectively. The overlapping regions 411, 413, and 415 are "region of interests". As shown in FIGS. 3A and 3B, the shape, depth, and location of the regions of interests can be controlled by changing the configurations of the two sources and the two detectors. The properties of the region of interests are calculated through the following equation:

$$\mu_a = w_{above}\mu_a^{above} + w_{below}\mu_a^{below} \quad (4)$$

With the same set up mentioned above, the amplitude of each measurement will be modulated by the arterial pulse as it changes the volume, thus the absorption to the light. Such change in the amplitude of measured signal can be correlated to the change in blood volume using the following equation:

$$\partial I^\lambda / <I^\lambda> = \left(\sum_{j=1}^M w_j^\lambda\right)\mu_a^\lambda \quad (5)$$

$<I^\lambda>$ is the averaged amplitude of measurement at wavelength $\lambda$, $\partial I^\lambda$ is the change in signal amplitude of ith measurement, $w_j^\lambda$ is the probability for photons to reach the ith location with artery inside tissue, $\mu_a^\lambda$ is the absorption of the arterial blood to the light. $w_j^\lambda$ is determined based upon above mentioned method which determines the absorption and scattering properties of tissue and the location of artery is determined through the tomographic scanning.

Figure 5:
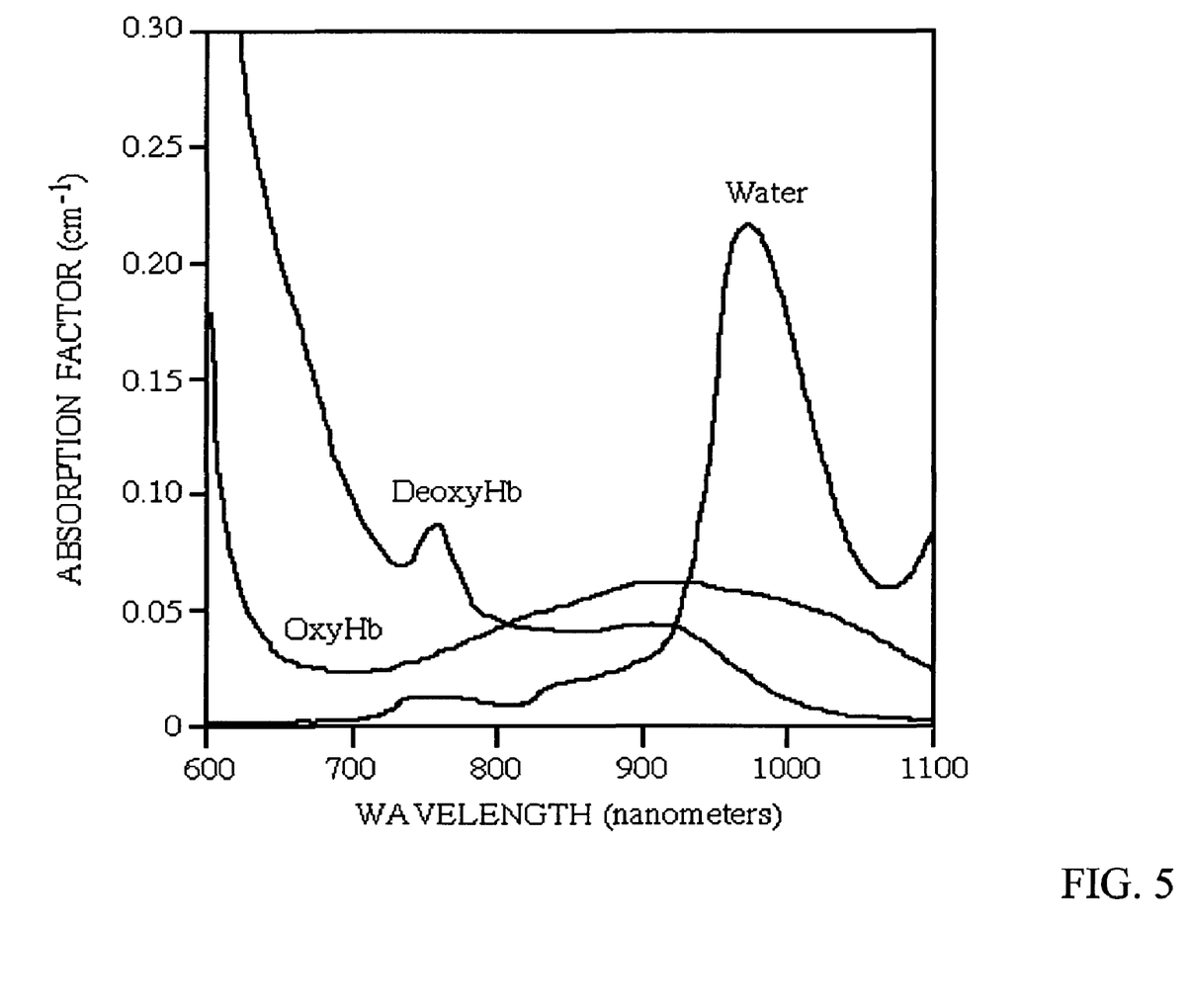
FIG. 5 shows the absorption spectrum of oxy-, deoxy-hemoglobin and water.

Once absorption properties of arterial blood at two or more wavelengths are known, the concentrations of chromophores can be determined through the following equation:

$$\mu_a^\lambda = \sum_{i=1}^N C_i \varepsilon_{i,\lambda} \quad (6)$$

where $C_i$ is the concentration of the ith chromophore, $\varepsilon_{i,\lambda}$ is the absorption extinction coefficient for the ith chromophore. If the total N chromophores have significant contribution to the signal, then at least N measurement at N different wavelengths are needed to solve Equation (6) in order to obtain the concentration of each chromophore. After obtaining the absorption properties of each element at each wavelength, the absorption spectrum of oxy-, deoxy-hemoglobin and water can be calculated through Equation (6) and based upon FIG. 5.

Figure 6A:
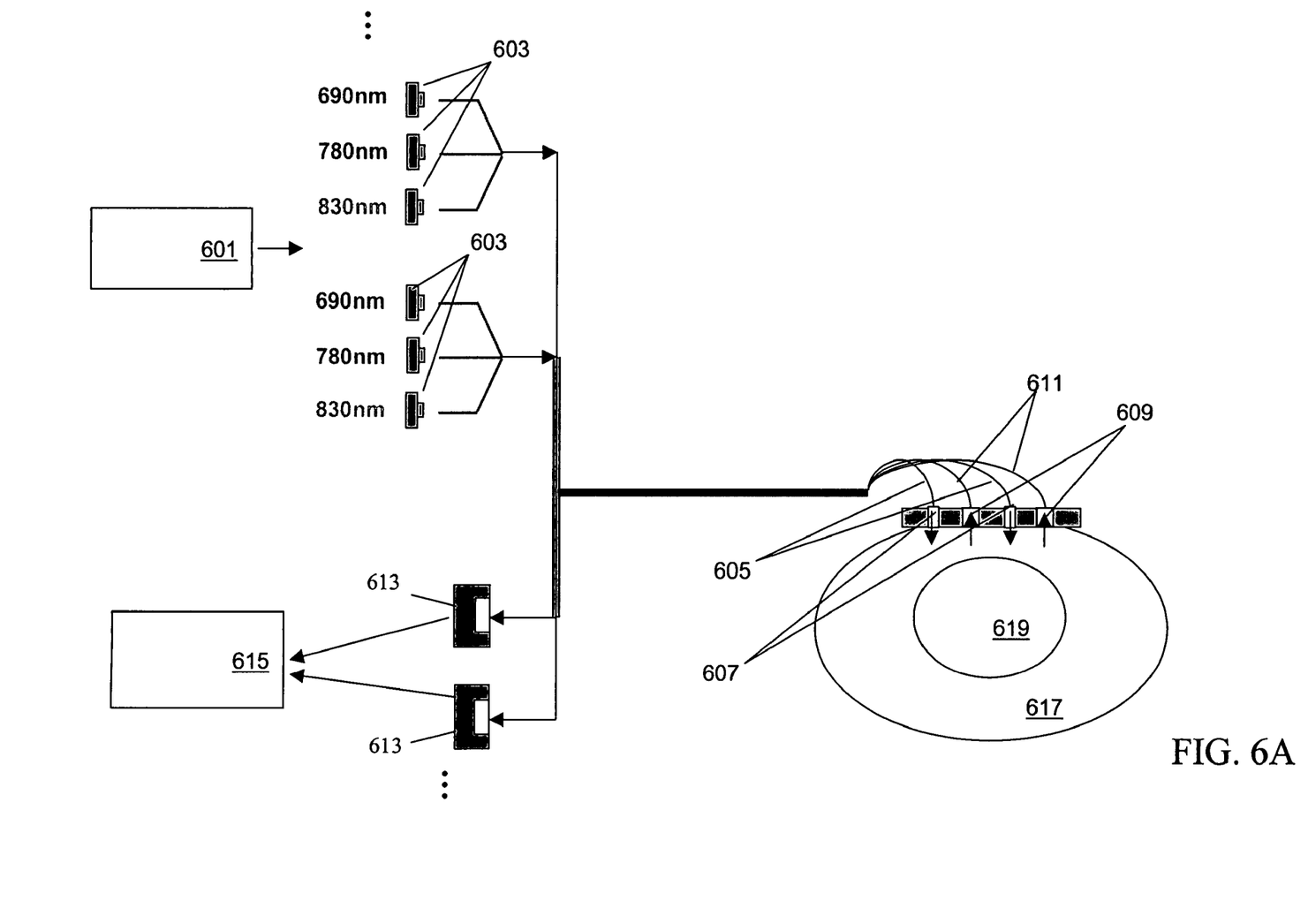
FIG. 6A illustrates a typical set-up for measuring hemoglobin concentration and oxygen saturation of brain tissues.

FIG. 6A depicts a typical set-up and measurement procedure to measure hemoglobin concentration and oxygen saturation of brain tissues based on the principles described above. Briefly, the oscillator power supply 601 activates laser diodes 603 to generate light waves of different wave lengths (e.g., 690 nm, 780 nm, and 830 nm). The light was guided through source fibers 605 and source probes 607 into the head tissue 617 and then brain 619. The detector probes 609 and detector fibers 611 guide the light that comes out of the head tissue 617 to the photo detectors 613. The intensity of each light source is modulated at two or more frequencies such as 100 MHz, 300 MHz, 500 MHz, etc. The local light intensity will oscillate at the same frequency as the source, but with a phase shift which depends on the absorption and scattering properties of the head tissue 617 and brain 619. Each detector 613 measures the phase shift between the received light and source light at each optical wavelength and at each modulation frequency. For each optical wavelength, the phase shifts between each source-detector fiber pair, at all modulations frequencies used to calculate the absorption and scattering properties of tissues that are scanned by such source-detector pair and at such wavelength. The calculation is performed by the signal processor 615 based upon Equation (1). As described above, the tissue medium will be divided into a number of volume elements. Each element may have same or different absorption and scattering properties. The phase measurement of each source-detector pair is related to the properties of each element through Equation (3).

If sufficient number of measurement is available, the property of each element can be obtained through solving a group of Equation (3). After obtaining the absorption properties of each element at each wavelength, the concentrations of oxy-, deoxy-hemoglobin can be calculated through Equation (6) and based upon the absorption characteristics of oxy-, deoxy-hemoglobin shown in FIG. 5.

Figure 7:
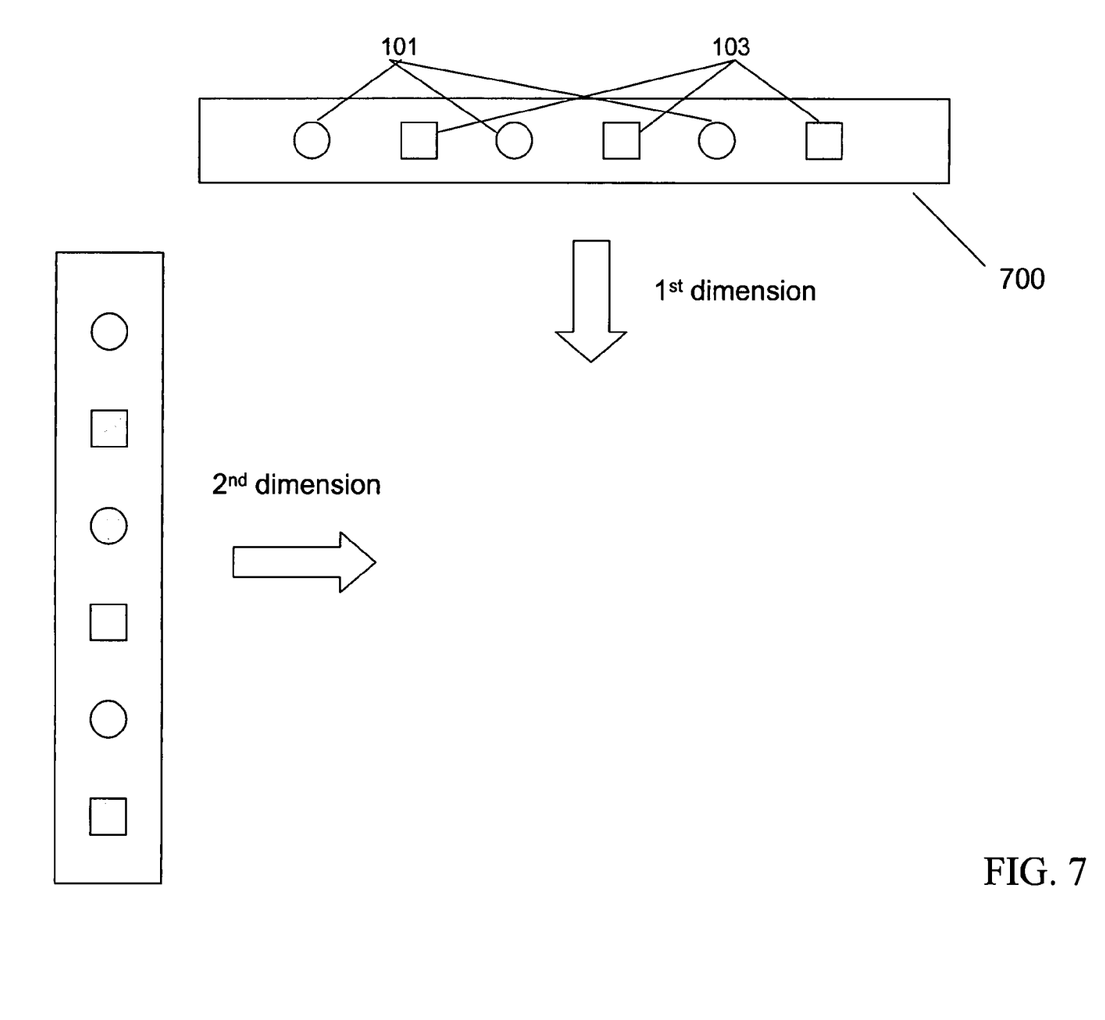
FIG. 7 illustrates a two-step measurement procedure for a two-dimensional structure using a one-dimensional wave source and detector array.
Figure 8:
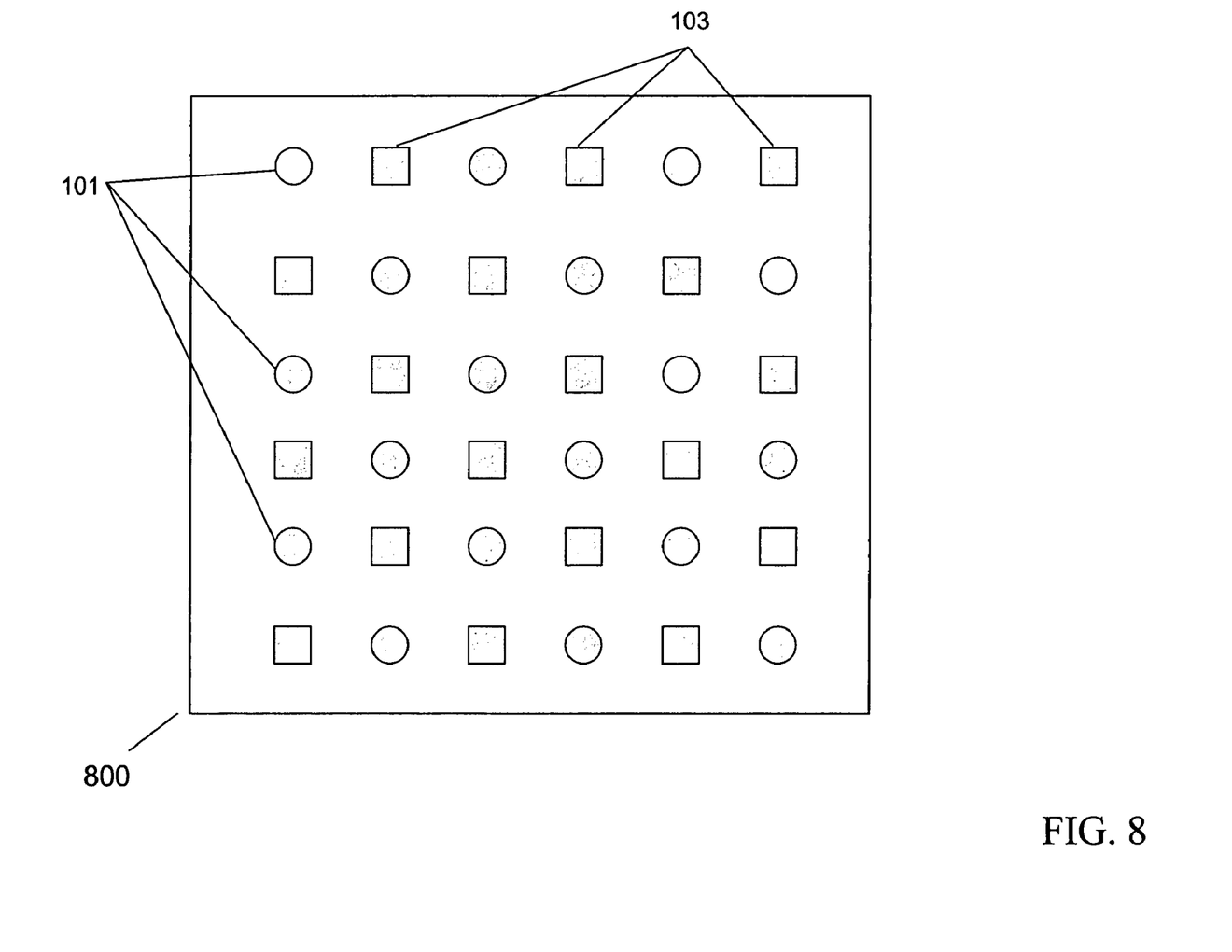
FIG. 8 shows a two-dimensional array of wave sources and wave detectors.

It should be noted that more than two wave source-detector pairs may be used for the measurement, and the wave source-detector configuration may vary. As shown in FIG. 7, the wave sources 101 and wave detectors 103 may form a one-dimension array 700 and the scan is performed in two dimensions by mechanically placing the wave source/detector array 700 in two positions that are perpendicular to each other. Alternatively, the scan may be performed using a two-dimensional array 800 of wave sources 101 and wave detectors 103 (FIG. 8).

Figure 6B:
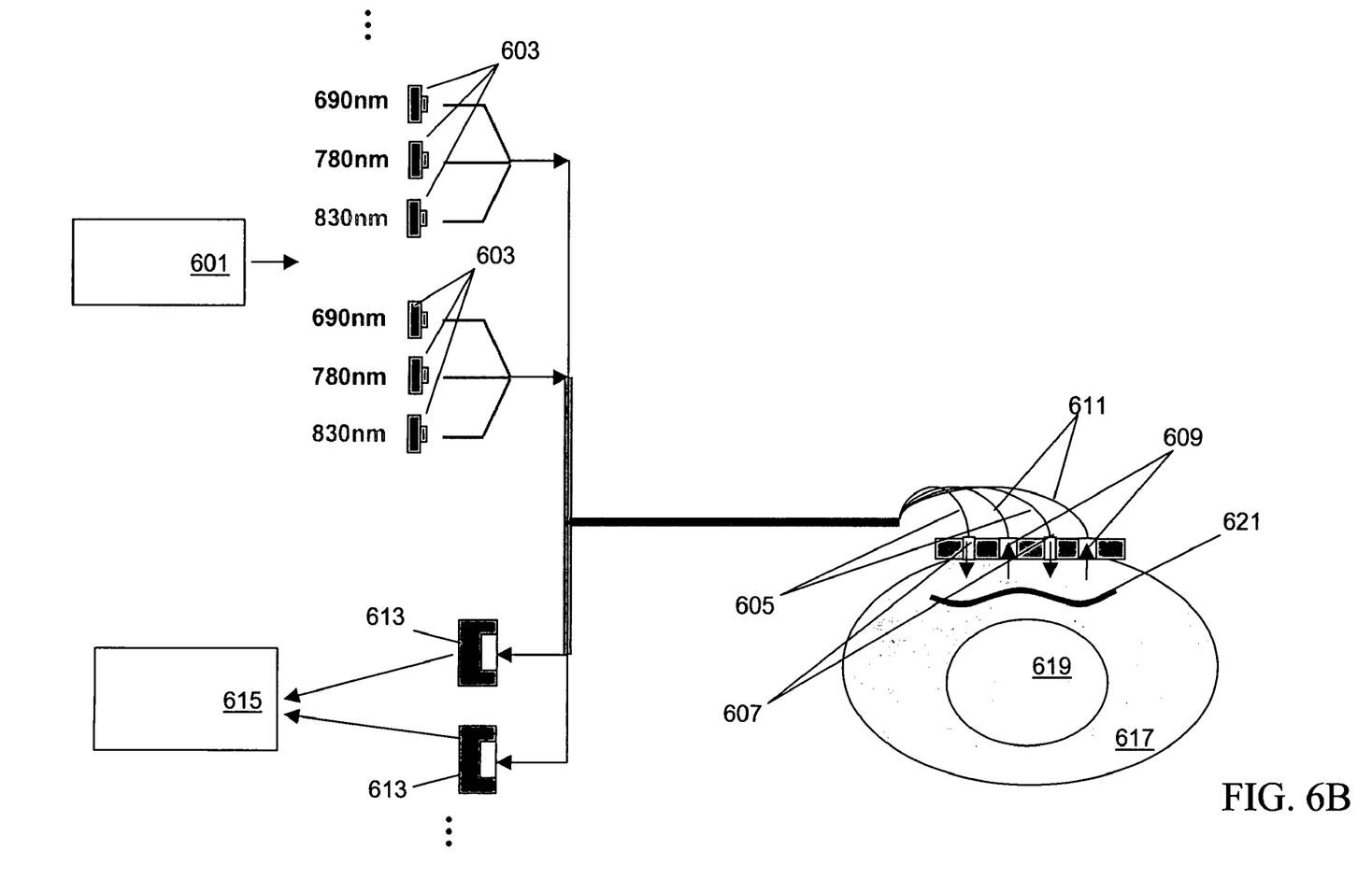
FIG. 6B illustrates typical set-up for measuring hemoglobin concentration and oxygen saturation of brain tissues, including brain arteries.

In another embodiment, the set-up of FIG. 6A can also be used to simultaneously measure oxy, deoxy-hemoglobin of brain tissue and in arterial blood. As shown in FIG. 6B, when there is an artery 621 under the wave source/detector array, the pulsation of artery will change local blood volume and thus the absorption to the light. Accordingly, the detected light intensity will change at the same frequency as the pulse. Such changes in the detected light intensity can be correlated to the absorption property of the arterial blood through Equation (5). By solving Equation (5) at multiple wavelengths, the concentrations of oxy-, deoxy-hemoglobin can be determined. Similarly, the concentrations of other substances, such as water, fat, cytochrome oxidase, carboxy hemoglobin can be determined using wavelengths in other spectrum windows.

The preferred embodiments of the device and method of the present invention are intended to be illustrative and not limiting. Modifications and variations can be made by persons skilled in the art in light of the above teachings. It is also conceivable to one skilled in the art that the present invention can be used for other purposes of measuring the acetone level in a gas sample, e.g. for monitoring air quality. Therefore, it should be understood that changes may be made in the particular embodiments disclosed which are within the scope of what is described as defined by the appended claims.

What is claimed is:

1. A method for quantifying at least one of scattering property, absorption coefficient or chromophore concentrations of a physical medium, said method comprising the steps of:
   (a) using a wave source, introducing into said physical medium, at a first site, an input modulated signal with a modulation frequency ($F_n$);
   (b) using a wave detector, detecting, at a second site, an output modulated signal migrated over a migration path in said physical medium from said input modulated signal;
   (c) comparing said output modulated signal with said input modulated signal and measuring therefrom a phase shift ($\phi$) between said input modulated signal and said output modulated signal;
   (d) repeating steps (a)-(c) at two or more modulation frequencies and calculating an average scattering property and absorption coefficient of said physical medium using the following equation:

$$\phi = \left(\sum_{n=0}^{1} a_n \mu_s'^n\right)\mu_a^{-1} + \left(\sum_{n=0}^{2} b_n \mu_s'^n\right)\mu_a^{-0.5} + \sum_{n=0}^{1} c_n \mu_s'^n$$

wherein $\mu_a$ is the absorption coefficient, $\mu_s'$ is the effective scattering property of said physical medium, and $a_n$, $b_n$, and $c_n$ are parameters determined by said modulation frequency ($F_n$) and a distance (D) between said first site and said second site using a fitting algorithm.

2. The method of claim 1, further comprising the step of positioning said wave source at said first site and said wave detector at said second site.

3. The method of claim 1, wherein said modulation frequency $F_n$ of said input waveform is higher than 50 MHz.

4. The method of claim 3, wherein said modulation frequency $F_n$ of said input modulated signal is about 100 MHz, 300 MHz, or 500 MHz.

5. The method of claim 1, wherein said input modulated signal has a wavelength of between about 600 nm and about 900 nm.

6. The method of claim 1, further comprising the step of determining the concentration of said chromophore using the following equation:

$$\mu_a^\lambda = \sum_{i=1}^{N} C_i \varepsilon_{i,\lambda}$$

wherein said $C_i$ is the concentration of said ith chromophore, $\varepsilon_{i,\lambda}$ is the absorption extinction coefficient for the ith chromophore, wherein N is the number of measurement at the different wavelengths when there are N total chromophores contributed to the signal.

7. A method for quantifying at least one of scattering property, absorption coefficient or chromophore concentrations of a physical medium, said method comprising the steps of:
   (a) positioning a source-detector pair on said physical medium, wherein said source-detector pair comprises a wave source and a wave detector, wherein said wave detector is placed at a distance (D) from said wave source;
   (b) introducing into said physical medium an input modulated signal with a modulation frequency ($F_n$) with said wave source;
   (c) detecting an output modulated signal migrated over a migration path in said physical medium from said input modulated signal with said wave detector;
   (d) comparing said output modulated signal with said input modulated signal and measuring therefrom a phase shift ($\phi$) between said input modulated signal and said output modulated signal;
   (e) repeating steps (a)-(d) at two or more modulation frequencies and calculating an average scattering property and absorption coefficient of said physical medium using the following equation:

$$\phi = \left(\sum_{n=0}^{1} a_n \mu_s'^n\right)\mu_a^{-1} + \left(\sum_{n=0}^{2} b_n \mu_s'^n\right)\mu_a^{-0.5} + \sum_{n=0}^{1} c_n \mu_s'^n$$

wherein $\mu_a$ is the absorption coefficient, $\mu_s'$ is the effective scattering property of said physical medium, $a_n$, $b_n$, and $c_n$ are parameters determined by said distance (D) of said wave source and said detector and said modulation frequency ($F_n$) using a fitting algorithm.

8. The method of claim 7, wherein said modulation frequency $F_n$ of said input modulated signal is higher than 50 MHz.

9. The method of claim 8, wherein said modulation frequency $F_n$ of said input modulated signal is about 100 MHz, 300 MHz, or 500 MHz.

10. The method of claim 7, wherein said input modulated signal has a wavelength of between about 600 nm and about 900 nm.

11. The method of claim 10, further comprising the step of: repeating steps (b) to (e) at two or more wavelengths.

12. The method of claim 11, wherein steps (b) to (e) are repeated at three wavelengths of about 690 nm, 720 nm and 830 nm.

13. The method of claim 11, further comprising the step of: determining an absorption spectrum of said physical medium.

14. The method of claim 7, further comprising the step of: determining the concentration of said chromophore in said physical medium using the following equation:

$$\mu_a^\lambda = \sum_{i=1}^{N} C_i \varepsilon_{i,\lambda}$$

wherein said $C_i$ is the concentration of said ith chromophore, $\varepsilon_{i,\lambda}$ is the absorption extinction coefficient for the ith chromophore, wherein N is the number of measurement at the different wavelengths when there are N total chromophores contributed to the signal.

15. The method of claim 7, further comprising:
dividing said physical medium into m volume elements;
performing step (a) to (e) j times with j source-detector pairs, wherein j is an integer that is equal to, or greater than 2; and determining a ratio of absorption coefficients and said effective scattering properties of said medium by using the following equations:

$$\mu_a^i = w_1^i \mu_{a,1}^i + w_2^i \mu_{a,2}^i + w_3^i \mu_{a,3}^i + \ldots + w_m^i \mu_{a,m}^i$$

$$\mu_s^i = w_1^i \mu_{s,1}^i + w_2^i \mu_{s,2}^i + w_3^i \mu_{s,3}^i + \ldots + w_m^i \mu_{s,m}^i$$

wherein i is the measurement of ith source-detector pair, $w_1^i$ is the weight of the first volume element corresponding to the ith source-detector pair; $w_2^i$ is the weight of the second volume element corresponding to the ith source-detector pair, and $w_m^i$ is the weight of the mth volume element corresponding to the ith source-detector pair.

16. The method of claim 7, wherein said physical medium is a biological tissue.

17. A method for quantifying at least one of scattering property, absorption coefficient or chromophore concentrations of a biological tissue using tomographic scanning, said method comprising the steps of:
(a) positioning a one-dimensional source-detector array on said biological tissue in a first position, wherein said one-dimensional source-detector array comprising at least two source-detector pairs, each said source-detector pair comprising a wave source and a wave detector, wherein said wave detector is placed at a distance (D) from said wave source; and wherein using each source-detector pair comprises the steps of:
   (i) introducing into said biological tissue an input modulated signal with a modulation frequency ($F_n$) with said wave source;
   (ii) detecting an output modulated signal migrated over a migration path in said biological tissue from said input modulated signal with said wave detector;
   (iii) comparing said output modulated signal with said input modulated signal and measuring therefrom a phase shift ($\phi$) between said input modulated signal and said output modulated signal;
   (iv) repeating steps (i)-(iii) at two or more modulation frequencies and calculating an average scattering property and absorption coefficient of said tissue using the following equation:

$$\phi = \left(\sum_{n=0}^{1} a_n \mu_s'^n\right)\mu_a^{-1} + \left(\sum_{n=0}^{2} b_n \mu_s'^n\right)\mu_a^{-0.5} + \sum_{n=0}^{1} c_n \mu_s'^n$$

wherein $\mu_a$ is the absorption coefficient, $\mu_s'$ is the effective scattering property of said biological tissue, and $a_n$, $b_n$, and $c_n$ are parameters determined by said distance (D) of said wave source and said detector and said modulation frequency ($F_n$) using a fitting algorithm; and
(b) positioning said one-dimensional source-detector array on said biological tissue in a second position, wherein said second position is perpendicular to said first position.

18. The method of claim 17, wherein said modulation frequency $F_n$ of said input modulated signal is higher than 50 MHz.

19. The method of claim 18, wherein said modulation frequency $F_n$ of said input modulated signal is about 100 MHz, 300 MHz, or 500 MHz.

20. A method for simultaneously determining a concentration of a biochemical substance in a biological tissue and in blood, said method comprising:

positioning multiple source-detector pairs on multiple locations of said biological tissue comprising an artery, wherein each source-detector pair comprises a wave source that produces an input modulated signal, and a wave detector that locates at a distance from said wave source and detects an output modulated signal;
determining concentrations of said biochemical substance in said biological tissue based on measurements of phase shift between the input modulated signal and corresponding modulated signal; and
determining a correlation between a change in an amplitude of said modulated signal and a change in blood volume using the following equation:

$$\partial I^\lambda / \langle I^\lambda \rangle = \left(\sum_{j=1}^{M} W_j^\lambda\right) \mu_a^\lambda$$

wherein $\langle I^\lambda \rangle$ is the averaged amplitude of measurement at wavelength $\lambda$, $\partial I^\lambda$ is the change in signal amplitude of ith measurement, $w_j^\lambda$ is the probability for photons to reach the ith location with artery inside the biological tissue, and $\mu_a^\lambda$ is the absorption of the arterial blood to the light.

21. The method of claim 20, further comprising the step of determining the concentration of an ith chromophore using the following equation:

$$\mu_a^\lambda = \sum_{i=1}^{N} C_i \varepsilon_{i,\lambda}$$

wherein said $C_i$ is the concentration of said ith chromophore, $\varepsilon_{i,\lambda}$ is the absorption extinction coefficient for the ith chromophore, and wherein N is the number of measurements at the different wavelengths when there are N total chromophores contributed to the signal.

22. The method of claim 20, wherein said substance is oxy-hemoglobin.

23. The method of claim 20, wherein said substance is deoxy-hemoglobin.

24. The method of claim 20, wherein said biological tissue consists of at least one of an organ, tissue, or body fluid.

25. The method of claim 24, wherein said biological tissue is one of a brain, heart, kidney, liver and vascular tissue which includes an artery, vein, and capillary.

26. An optical system for quantifying at least one of scattering property, absorption coefficient or chromophore concentrations of highly scattering physiological medium by using phase-only measurement comprising:
a wave source configured to be optically coupled with said physiological medium for irradiating at least two electromagnetic waves having different wavelengths, wherein the intensity of said wave source has at least two modulation frequencies;
a wave detector, placed at a distance from said wave source, for detecting said at least two electromagnetic waves from said wave source and generating at least two output signals in response thereto, wherein said wave detector is capable of determining a phase shift between said introduced and detected radiation at a first wavelength and a second wavelength, and at a first modulation frequency and a second modulation frequency;
a processor configured to operatively couple with said wave detector and to determine a scattering property and absorption coefficient of said physiological medium based on a phase (φ) only measurement using the following equation:

$$\phi = \left(\sum_{n=0}^{1} a_n \mu_s'^n\right)\mu_a^{-1} + \left(\sum_{n=0}^{2} b_n \mu_s'^n\right)\mu_a^{-0.5} + \sum_{n=0}^{1} c_n \mu_s'^n$$

wherein $\mu_a$ is the absorption coefficient, $\mu_s'$ is the effective scattering property of said physiological medium, $a_n$, $b_n$, and $c_n$ are parameters determined by said distance (D) of said wave source and said detector and said modulation frequency ($F_n$) using a fitting algorithm.

27. The optical system of claim 26, wherein said wave source has wavelengths between the range of 500-2500 nm.

28. The optical system of claim 27, wherein said wave source has wavelengths between the range of 600-900 nm.

29. The optical system of claim 26, wherein said modulation frequency of said electromagnetic wave is higher than 50 MHz.

30. The optical system of claim 29, wherein said modulation frequency ($F_n$) of said input signal is about 100 MHz, 300 MHz, or 500 MHz.

31. The optical system of claim 26, wherein said physiological medium is a biological tissue.

32. The optical system of claim 26, further comprising two or more wave source-detector pairs, wherein each of said wave source produces electromagnetic waves with at least two wavelengths and at least two modulation frequencies to said physiological medium.

33. The optical system of claim 32, wherein said processor is configured to determine a ratio of said absorption coefficients and said effective scattering properties of said medium by arbitrarily dividing said medium into m volume elements, and calculating the ratio of said absorption coefficients and said effective scattering properties of said medium by using the following equations:

$$\mu_a^i = w_1^i \mu_{a,1}^i + w_2^i \mu_{a,2}^i + w_3^i \mu_{a,3}^i + \ldots + w_m^i \mu_{a,m}^i$$

$$\mu_s^i = w_1^i \mu_{s,1}^i + w_2^i \mu_{s,2}^i + w_3^i \mu_{s,3}^i + \ldots + w_m^i \mu_{s,m}^i$$

wherein i is the measurement of ith source-detector pair, $w_1^i$ is the weight of the first volume element corresponding to the ith source-detector pair; $w_2^i$ is the weight of the second volume element corresponding to the ith source-detector pair, and $w_m^i$ is the weight of the mth volume element corresponding to the ith source-detector pair.

34. A method for determining concentrations of oxygenated hemoglobin and deoxygenated hemoglobin in a biological tissue or in blood comprising the steps of:
applying said optical system of claim 26 to a medium; and
monitoring at least one of oxygenated hemoglobin concentration, deoxygenated hemoglobin concentration and a ratio thereof.

35. The method of claim 34, further comprising the step of:
determining a presence of an ischemic condition over a finite area of a biological tissue.

36. The method of claim 34, further comprising the step of detecting the location of an artery.

37. The method of claim 34, wherein said biological tissue consists of one of a brain, heart, kidney, liver and vascular tissue which includes an artery, vein, and capillary.

38. The method of claim 34, wherein said biological tissue further includes transplanted cells.

39. A method for diagnosing a tumor in a biological tissue comprising the steps of:

applying said optical system of claim 26 to said biological tissue; and
determining the presence of tumor cells over a finite area of said biological tissue.

40. A optical system for simultaneously determining a concentration of a biochemical substance in a biological tissue and in blood comprising:
at least two source-detector pairs configured to be on at least two locations of a medium of said biological tissue, wherein each said pair of source-detector comprises:
a wave source that produces an input modulated signal having different wavelengths, wherein the intensity of said each wave source has at least two modulation frequencies,
a wave detector that locates at a distance from said wave source and detects an output modulated signal; wherein said wave detector is capable of determining concentrations of said biochemical substance in said biological tissue based on measurements of phase shift between input modulated signal and corresponding output modulated signal, wherein said wave detector is also capable of measuring an amplitude of an electromagnetic wave;
a processor configured to operatively couple with said wave detector and to determine a correlation between a change in an amplitude of said electromagnetic waveform and a change in blood volume using the following equation:

$$\partial I^\lambda / \langle I^\lambda \rangle = \left(\sum_{j=1}^{M} W_j^\lambda\right)\mu_a^\lambda$$

wherein $\langle I^\lambda \rangle$ is the averaged amplitude of measurement at wavelength λ, $\partial I^\lambda$ is the change in signal amplitude of ith measurement, $w_j^\lambda$ is the probability for photons to reach the ith location with artery inside the biological tissue, and $\mu_a^\lambda$ is the absorption of the arterial blood to the light.

41. The optical system of claim 40, wherein said wave source has wavelengths between the range of 600-900 nm.

42. The optical system of claim 40, wherein said modulation frequency of said electromagnetic wave is higher than 50 MHz.

43. The optical system of claim 40, wherein said processor is capable of determining the concentration of an ith chromophore using the following equation:

$$\mu_a^\lambda = \sum_{i=1}^{N} C_i \varepsilon_{i,\lambda}$$

wherein said $C_i$ is the concentration of said ith chromophore, $\varepsilon_{i,\lambda}$ is the absorption extinction coefficient for the ith chromophore, wherein N is the number of measurements at the different wavelengths when there are N total chromophores contributed to the signal.

44. A method for determining concentrations of oxygenated hemoglobin deoxygenated hemoglobin in a biological tissue or blood comprising the steps of:
applying said optical system of claim 40 to said biological tissue; and monitoring at least one of oxygenated hemoglobin concentration, deoxygenated hemoglobin concentration and a ratio thereof.

45. The method of claim 44, further comprising the step of: determining a presence of an ischemic condition over a finite area of said biological tissue.

46. The method of claim 44, further comprising the step of detecting the location of an artery.

47. The method of claim 44, wherein said biological tissue consists of one of a brain, heart, kidney, liver and vascular tissue which includes an artery, vein, and capillary.

48. The method of claim 47, wherein said biological tissue further includes transplanted cells.

* * * * *